(12) United States Patent
Bass et al.

(10) Patent No.: US 7,220,879 B2
(45) Date of Patent: May 22, 2007

(54) METHOD FOR INHIBITING POLYMERIZATION OF (METH)ACRYLIC ACID AND ITS ESTERS USING AN INHIBITOR AND A PROCESS FOR MAKING A COMPOUND USEFUL AS SUCH AN INHIBITOR

(75) Inventors: Stephen Bass, Pearland, TX (US); Robert Michael Mason, Houston, TX (US); Joy Lyndon Mendoza, Seabrook, TX (US); Steven John Skoog, Houston, TX (US); Mark T. Vandersall, Jamison, PA (US)

(73) Assignee: Rohm and Haas Company, Philadelphia, PA (US)

( * ) Notice: Subject to any disclaimer, the term of this patent is extended or adjusted under 35 U.S.C. 154(b) by 74 days.

(21) Appl. No.: 11/229,916

(22) Filed: Sep. 19, 2005

(65) Prior Publication Data

US 2006/0074257 A1 Apr. 6, 2006

Related U.S. Application Data

(60) Provisional application No. 60/615,230, filed on Oct. 1, 2004.

(51) Int. Cl.
*C07C 69/52* (2006.01)
*C07C 57/02* (2006.01)
(52) U.S. Cl. .................. 560/205; 562/598
(58) Field of Classification Search .............. None
See application file for complete search history.

(56) References Cited

U.S. PATENT DOCUMENTS

| | | | |
|---|---|---|---|
| 2,675,359 A | 4/1954 | Schneider | |
| 2,723,245 A | 11/1955 | Wheaton | |
| 3,641,016 A | 2/1972 | Korosi et al. | |
| 4,021,310 A | 5/1977 | Shimizu et al. | |
| 4,025,467 A | 5/1977 | Brock | |
| 4,129,534 A | 12/1978 | Cunningham | |
| 4,221,871 A | 9/1980 | Meitzner et al. | |
| 4,813,974 A | 3/1989 | Morris et al. | |
| 5,693,680 A | 12/1997 | McQuigg | |
| 6,458,989 B1 | 10/2002 | Aichinger et al. | |

FOREIGN PATENT DOCUMENTS

DE 1946823 4/1971

OTHER PUBLICATIONS

Smith, M. and March, J., *March's Advanced Organic Chemistry: Reactions, Mechanisms, and Structure*, 5th Ed., 2001, John Wiley & Sons, Inc., New York, p. 310.
R. Raue in *Ullmans Encyclopedia of Industrial Chemistry*, 5th Ed., 1985, VCH Deerfield Beach FL, vol. A3, p. 213.
The Merck Index, 11th Addition, 1989, Merck & Co., Rahway New Jersey, p. 954.
Kirk-Othmer *Encyclopedia of Chemical Technology*, vol. 3, 4th addition, 1992, John Wiley & Sons, New York p 814.
*Ullmann's Encyclopedia of Industrial Chemistry*, 5th completely revised edition, vol. A9 VCH, Deerfield Beach, Florida, p. 107.
Database CA 'Online! Chemical Abstracts Service, Columbus, Ohio, US; Apr. 22, 2001, Nerenberg, C. et al: "Purification of thionine, Azure A, Azure B., and methylene blue" XP002364859.

*Primary Examiner*—Paul A Zucker
(74) *Attorney, Agent, or Firm*—Marcella M. Bodner

(57) ABSTRACT

This invention relates to a method for inhibiting polymerization of (meth)acrylic acid and its esters using a polymerization inhibitor which comprises at least one reduced halide-content azine dye-based compound. A process for producing reduced halide-content azine dye-based compounds using ion exchange resin technology is also provided.

5 Claims, 1 Drawing Sheet

METHOD FOR INHIBITING POLYMERIZATION OF (METH)ACRYLIC ACID AND ITS ESTERS USING AN INHIBITOR AND A PROCESS FOR MAKING A COMPOUND USEFUL AS SUCH AN INHIBITOR

CROSS REFERENCE TO RELATED PATENT APPLICATIONS

This is a non-provisional patent application of co-pending U.S. provisional patent application Ser. No. 60/615,230 filed Oct. 1, 2004.

The present invention relates to a method for inhibiting polymerization of (meth)acrylic acid and its esters, for example during separation and purification processes, using a polymerization inhibitor. The present invention also relates to an ion exchange resin process for making reduced halide-content azine dye-based compounds which are suitable for use as a polymerization inhibitor.

BACKGROUND

When (meth)acrylic acid and its esters are prepared by conventional reaction processes, these products are generally present in a mixed product gas exiting the reactors of such processes. Typically, mixed product gases containing (meth)acrylic acid are cooled and contacted with an aqueous stream in an absorption tower, thereby providing a crude product stream which is then purified, often by dehydration in a distillation step, to provide a more concentrated and pure product solution. Mixed product gases containing esters of (meth)acrylic acid are generally non-aqueous streams, often with alcohols as the solvent-carrier, which are also subjected to purification by distillation, which also results in formation of a more concentrated and pure product solution.

Unfortunately, under the high temperature conditions typical of purification by, distillation, (meth)acrylic acid and its esters have a strong tendency to polymerize, creating unwanted polymer solids in the process equipment. It is important to prevent such unwanted polymerization of (meth)acrylic acid and its esters because process equipment may become blocked and clogged with the polymer solids which tends to interfere, sometimes dangerously, with ongoing operation of the purification process. In addition, loss of product yield often results from the polymerization of a portion of the product.

One established method for inhibiting polymerization of (meth)acrylic acid and its esters involves addition of one or more substances, which inhibit such polymerization, to the process streams and process equipment during separation and purification operations. More particularly, polymerization inhibitors that comprise methylene blue (tetramethylthionine chloride), along with one or more other compounds, such as hydroquinone (HQ) and phenothiazine (PTZ), have been found to provide good polymerization inhibiting effects for (meth)acrylic acid and its esters.

For example, such a method was described in U.S. Pat. No. 4,021,310, which teaches the addition of a combination of three substances to a distillation column during separation and purification of a crude aqueous stream containing acrylic acid or its esters. More particularly, the distillation was carried out in the presence of a three-component inhibitor system comprising: (A) at least one compound selected from the group consisting of hydroquinone, hydroquinonemonomethyl ether, cresols, phenols, t-butyl catechol, diphenylamine, phenothiazines and methylene blue; (B) at least one compound selected from the group consisting of copper dimethyldithiocarbamate, copper diethyldithiocarbamate copper dibutyldithiocarbamate and copper salicylate; and (C) molecular oxygen. According to the disclosure of this patent, this method achieved a synergistic polymerization inhibiting effect when the aforesaid compounds were simultaneously present in the distillation of aqueous streams containing acrylic acid and its esters.

However, it has also been learned that the halide (i.e., chloride) anions in methylene blue compound tend to corrode separation and purification process equipment constructed of low nickel content stainless steel, including but not limited to those grades containing less than about 35 weight percent nickel, such as grades 304, 316, and 317L. Although metal alloys and coatings (e.g., glass) that are resistant to chloride corrosion are commercially available, their costs are significantly higher than low nickel content stainless steel and are, therefore, less attractive substitutes for constructing commercial process apparatus. Furthermore, unless specifically removed with the attendant additional costs of such removal, the chloride of methylene blue will continue to cause negative effects in process apparatus downstream of the separation and purification portion, through corrosion and other unwanted interactions with these less expensive materials of construction.

Thus, removal and/or substitution of a substantial portion of the chloride (i.e., halide) anions in methylene blue (a thiazine dye-based compound) would provide reduced halide-content thiazine-based compounds that are suitable for use as polymerization inhibitors having reduced corrosion and other unwanted effects. Similarly, since methylene blue is a member of the class of compounds known as azine dyes, which includes thiazine-, oxazine-, and diazine dye-based compounds, removal and/or substitution of a substantial portion of the halide anions in azine-based compounds would provide various reduced halide-content azine dye-based compounds suitable for use as polymerization inhibitors in processes for separation and purification of (meth) acrylic acid and its esters.

Suitable reduced halide-content azine-based compounds may be available in readily usable form from various commercial sources. For example, 5-amino-4-(diethylamino)benzo[a]-phenoxazinium hydrogen sulfate (Nile Blue A) (which has an oxazine dye-based cation) or 3,7-Diaminophenothizain-5-ium acetate (thionine acetate) (which has a thiazine dye-based cation) are commercially available and suitable inhibitor compounds which would be expected to inhibit polymerization of (meth)acrylic acid and its esters. Since these compounds are of reduced halide-content, they would also be expected to provide polymerization inhibiting effects while reducing corrosion of process equipment compared to compounds containing halides, such as chloride. Furthermore, such inhibitor compounds having azine dye-based cations are suitable for use alone or with other compounds, such as those mentioned above, which also have polymerization inhibiting activity.

It is also desirable to be able to convert halide-containing azine dye-based compounds, such as, for example, tetramethylthionine chloride (methylene blue), into reduced halide-content azine-based compounds suitable for use as polymerization inhibitors, either alone or with other inhibitor compounds. An ion exchange process, wherein the halide anions of such azine dye-based compounds are exchanged for another less-corrosive anion species, would achieve the aforesaid desired conversion. Generally, ion exchange processes exchange one ion in solution for another ion that is bound to a substrate.

For example, U.S. Pat. No. 3,641,016 discloses methods for preparing thionine derivatives using ion exchange processes conducted in solution, which do not involve ion exchange resins and, therefore, require additional drying, filtration, and/or washing steps to remove the solvent and unwanted inorganic alkaline salts from the final thionine derivative products. In particular, Example 13 of U.S. Pat. No. 3,641,016 describes the formation of the hydroxide form of thionine compounds by treatment with a strong base, i.e., potassium hydroxide or sodium hydroxide, in alcoholic solution. The solution is dried by evaporation and the alkaline salt is removed by washing the solids with a small quantity of water, leaving the purified, dry thionine hydroxide product. Example 14 of U.S. Pat. No. 3,641,016 describes the formation of thionine salts having organic and mineral acids (such as acetates, fumarates, halogens, and sulfates) by an ion exchange process wherein the hydroxy groups of the thionine hydroxide compounds, in either aqueous or alcoholic solution, are replaced by the preferred organic or mineral acid anions. Where aqueous solutions are used, the newly formed thionine compound is separated from the solution by filtration and removal of additional organic and inorganic alkaline salts is achieved by washing with a small quantity of water. Where the solution is alcoholic, after the hydroxy groups of the thionine hydroxide compounds are replaced by the preferred organic or mineral acid anions, the solution must be dried, as by evaporation, to collect the solids, which are then washed with a small quantity of water to remove the inorganic alkaline salts. In addition, Example 15 of U.S. Pat. No. 3,641,016 discusses the preparation of thionine derivatives having anions derived from carboxylic acids by an ion exchange in aqueous solution between the thionine chloride, bromide or perchlorate compound and the sodium, potassium or ammonium salt of the desired carboxylic acid. The filtration and washing steps are also required in this process to separate and purify the resulting carboxylic acid form of the thionine compound.

It is also noted that U.S. Pat. No. 6,458,989 discloses the use of sulfonic salts as inhibitors in the production of (meth)acrylic acid and its esters, however, only sulfonic salts of phenothiazine are illustrated in the examples. Furthermore, while phenothianzine is a compound belonging to the class of compounds known as azines, phenothiazine is not an azine dye-based compound, with which the present invention is concerned. See Smith, M. and March, J., *March's Advanced Organic Chemistry: Reactions, Mechanisms, and Structure*, 5$^{th}$ Ed., 2001, John Wiley & Sons, Inc., New York, p. 310; and R. Raue in *Ullmans Encyclopedia of Industrial Chemistry*, 5$^{th}$ Ed., 1985, VCH Deerfield Beach Fla., Vol. A3, p. 213.

Various suitable resin substrates are known in the industry and are conventionally made from polymer material or zeolites. While ion exchange processes, and the ion exchange resins used in such processes, are generally known and developed for application in various fields, there are a number of difficulties encountered with such processes as particularly applied to the conversion of azine dye-based compounds.

For example, U.S. Pat. No. 4,813,974 describes an ion exchange process which reduces the halide (e.g., chloride) content of cationic or basic dyes, such as tetramethylthionine chloride, but the disclosed process is designed to remove only the stoichiometric excess halide anions. Although the use of strongly basic ion exchange resins would be a clear way to remove halide ions associated with the dye molecules, U.S. Pat. No. 4,813,974 warns against the use of strongly basic ion exchange resins due to the resulting high pH which tends, in turn, to render the resulting salt product highly unstable. U.S. Pat. No. 4,813,974 explains how to avoid removing too much halide by matching the total capacity of the ion exchange resin loaded into the reactor with the excess halide content of a single batch of dye being treated, which necessarily results in leaving the stoichiometric halide in the dye. Thus, while U.S. Pat. No. 4,813,974 suggests that all or any portion of the halide anions directly associated with the cation portion of the starting compound may be removed and subsequently replaced with substitute anions, that patent warns that this may be achieved only if the temporary exposure to the resulting higher pH does not adversely affect the cation portion and does not provide any information or guidance as to how to avoid or mitigate such adverse affect. Thus, U.S. Pat. No. 4,813,974 does not explain how to successfully address the difficulties and obstacles of which it warns.

In addition, it has been known in the art that methylene blue is considered to be incompatible with basic conditions (i.e., high pH environments). See The Merck Index, 11$^{th}$ Addition, 1989, Merck & Co., Rahway N.J., p. 954. Furthermore within the dye industry, azine-based dyes, of which methylene blue is a member, are classified as basic dyes (i.e., the chromophore is cationic). See *Kirk-Othmer Encyclopedia of Chemical Technology*, Vol. 3, 4$^{th}$ addition, 1992, John Wiley & Sons, New York p 814. As indicated in *Ullmann's Encyclopedia of Industrial Chemistry*, 5$^{th}$ completely revised edition, Volume A9 VCH, Deerfield Beach, Fla., p. 107, members of this class of dyes are generally considered to be sensitive to basic conditions because sodium hydroxide has been reported to change or decolorize solutions of basic dyes (i.e., the cation portion is destroyed). Thus, persons of ordinary skill are dissuaded, by the general knowledge and information in the art, from using ion exchange resins with a high pH environment to synthesize derivatives of azine dye-based compounds, including derivatives having reduced halide content.

Notwithstanding the foregoing, the present invention provides a method of inhibiting polymerization of (meth)acrylic acid and its esters, for example during separation and purification processes, as well as transport and storage, using a polymerization inhibitor which comprises at least one reduced halide-content azine dye-based compound.

The present invention also provides a process for preparing reduced halide-content azine dye-based compounds using ion exchange resin technology, which addresses and overcomes the difficulties of known ion exchange processes discussed above.

SUMMARY

The present invention relates to a method for inhibiting polymerization of (meth)acrylic acid and its esters comprising the steps of: (A) providing a product comprising at least one compound selected from the group consisting of (meth) acrylic acid and its esters; and (B) adding an amount of a polymerization inhibitor to said product, said amount being sufficient to inhibit polymerization of said product and said polymerization inhibitor comprising at least one reduced halide-content azine dye-based compound having a cationic component and an anionic component. The at least one reduced halide-content azine dye-based compound has the general formula:

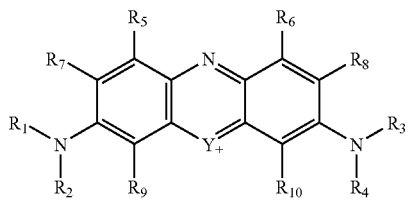

wherein

Y is selected from the group consisting of S, O, or NR*, where R* is selected from the group consisting of hydrogen, and saturated, unsaturated and substituted hydrocarbons;

$R_1$-$R_4$ are the same or different from one another; $R_5$-$R_{10}$ are the same or different from one another; and each of $R_1$-$R_{10}$ is selected from the group consisting of hydrogen, and saturated, unsaturated and substituted hydrocarbons; and X comprises at least one mono-, di- or tri-anion in a 1, 1/2, or 1/3 ratio respectively to the cationic component.

In a particular embodiment, the reduced halide-content azine dye-based compound may be selected from the group consisting of: tetramethylthionine sulfate, tetramethylthionine acetate, tetramethylthionine maleate, tetramethylthionine formate, and tetramethylthionine phthalate. Additionally, the polymerization inhibitor may further comprise at least one additional compound capable of inhibiting polymerization of (meth)acrylic acid and its esters.

In another embodiment, the method of the present invention may further comprise the steps of: (A) introducing said product to said distillation apparatus; (B) introducing said polymerization inhibitor to said distillation apparatus; and (C) distilling said product in said distillation apparatus, in the presence of said polymerization inhibitor, to form a purified product.

The present invention also relates to a process for preparing reduced halide-content azine dye-based compounds and comprises the steps of: (A) contacting at least one halide-containing azine dye-based compound with a basic ion exchange resin capable of absorbing halide anions and donating hydroxide anions to produce a halide-enriched ion exchange resin and a quantity of azine dye-based hydroxide compound, wherein the at least one halide-containing azine dye-based compound has the general formula:

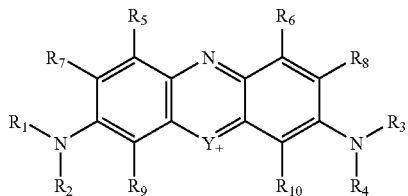

wherein

Y is selected from the group consisting of S, O, or NR*, where R* is selected from the group consisting of hydrogen, and saturated, unsaturated and substituted hydrocarbons;

$R_1$-$R_4$ are the same or different from one another; $R_5$-$R_{10}$ are the same or different from one another; and each of $R_1$-$R_{10}$ is selected from the group consisting of hydrogen, and saturated, unsaturated and substituted hydrocarbons; and X comprises at least one halide anion selected from the group consisting of chloride, bromide, iodide, and fluoride; and (B) contacting the quantity of azine dye-based hydroxide compound, within no more than about, 12 hours of termination of step (A), with an acid compound capable of removing the hydroxide and donating an anion to form a quantity of reduced halide-content azine dye-based compound having no greater than 4 weight percent of non-covalently bound halide, based on the total dry weight of said reduced halide-content azine dye-based compound. The acid compound may be selected from the group consisting of sulfuric acid, acetic acid, maleic acid, formic acid, and phthalic acid.

In one embodiment, the process of the present invention may further comprise preconditioning a non-hydroxide basic anion exchange resin with caustic to produce a basic ion exchange resin capable of absorbing halide anions and donating hydroxide anions, prior to contacting step (A).

The present invention also relates to a process for preparing reduced halide-content azine dye-based compounds, comprising the steps of: (A) preconditioning a basic ion exchange resin in hydroxide form with an acid compound capable of removing hydroxide anions and donating other anions to produce a basic ion exchange resin capable of absorbing halide anions and donating said other anions; and (B) contacting at least one halide-containing azine dye-based compound with said basic ion exchange resin capable of absorbing halide anions and donating said other anions to produce a quantity of reduced halide-content azine dye-based compound having a ratio of one mole of cations to less than 0.5 moles of non-covalently bound halogen anions, wherein said at least one halide-containing azine dye-based compound has the general formula:

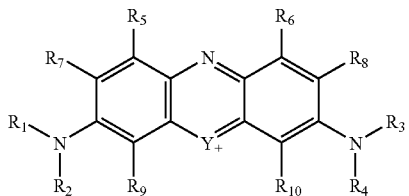

wherein

Y is selected from the group consisting of S, O, or NR*, where R* is selected from the group consisting of hydrogen, and saturated, unsaturated and substituted hydrocarbons;

$R_1$-$R_4$ are the same or different from one another; $R_5$-$R_{10}$ are the same or different from one another; and each of $R_1$-$R_{10}$ is selected from the group consisting of hydrogen, and saturated, unsaturated and substituted hydrocarbons; and X comprises at least one halide anion selected from the group consisting of chloride, bromide, iodide, and fluoride.

BRIEF DESCRIPTION OF THE DRAWINGS

For a better understanding of the present invention, reference is made to the following detailed description, considered in conjunction with the accompanying drawing, in which.

DETAILED DESCRIPTION

Figure 1:
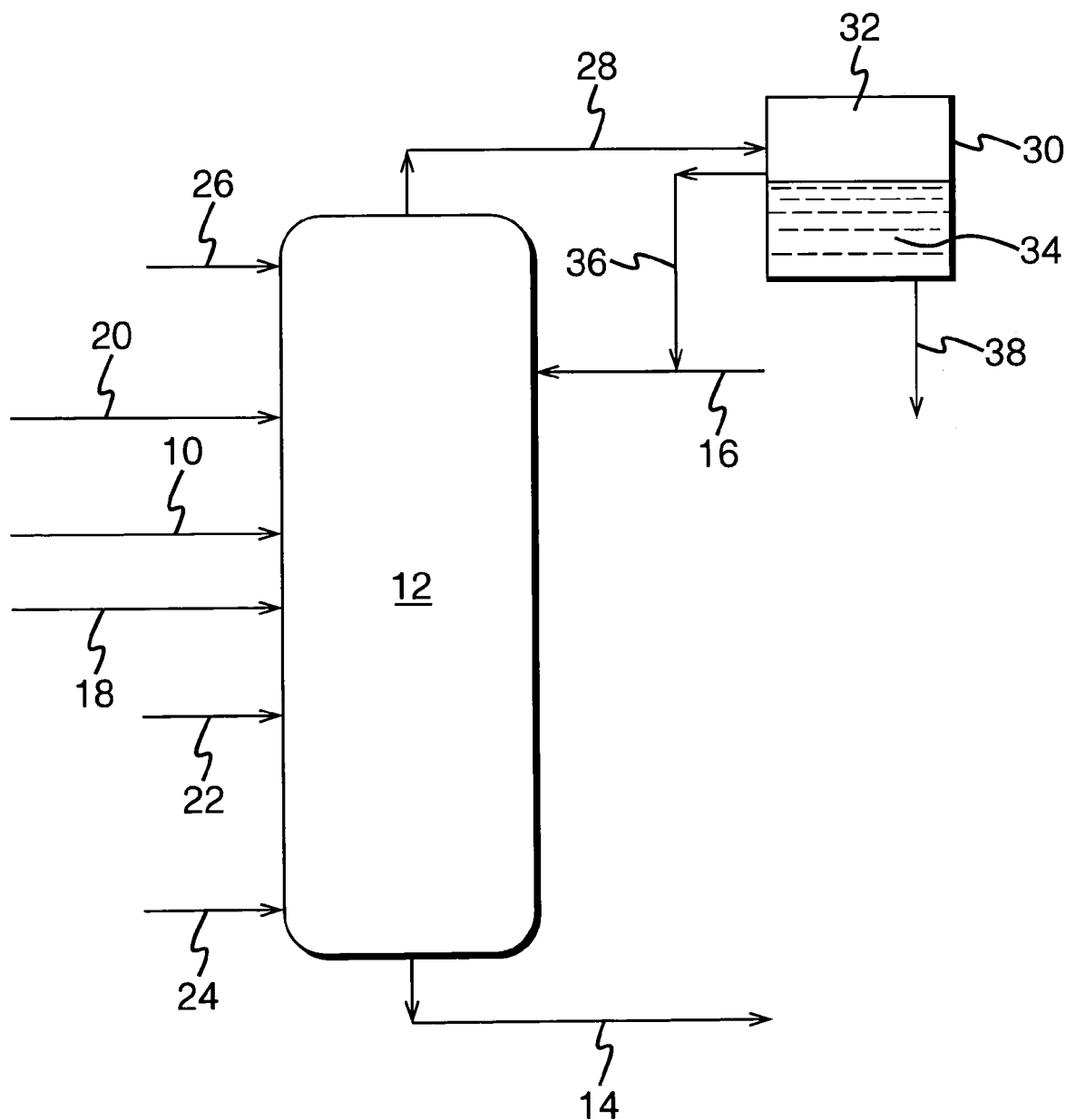
FIG. 1 is a schematic representation of a separation and purification process which employs the method of the present invention.

Throughout this specification and claims, unless otherwise indicated, references to percentages are by weight percent and all temperatures are in degrees centigrade (° C.).

It is also to be understood that for purposes of this specification and claims that the range and ratio limits, recited herein, are combinable. For example, if ranges of 1-20 and 5-15 are recited for a particular parameter, it is understood that ranges of 1-15 or 5-20 are also contemplated.

The term azine dye-based compounds (as distinguished from azine compounds in general), as used herein, means molecules having the following general molecular structure:

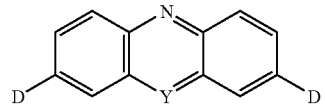

wherein Y may be —O—, —S—, or —NR— (R=hydrogen, alkyl, aryl, etc.); and D may be auxochrome groups such as an amino, arylamino, monoalkylamino, dialkylamino, or hydroxyl group. (see, e.g., R. Raue in *Ullmans Encyclopedia of Industrial Chemistry*, 5$^{th}$ Edition, 1985, VCH Deerfield Beach Fla., Vol. A3, p 213). It is believed that the auxochrome group functions as a group that displaces, through resonance, the absorption chromophor present in the azine molecule (see J. March and M. Smith in Advanced Organic Chemistry 5$^{th}$ Edition, 2001, Wiley, N.Y., p 310).

As used herein, the term "reduced halide-content" when used to describe an azine dye-based compound means that the compound contains halide anions (i.e., chloride, bromide, iodide, or fluoride anions), which are not covalently bonded to the compound, in a ratio of 1 mole of cations to no more than 0.5 moles of anions. In the case of methylene blue this corresponds to about 4 percent by weight (wt %) chloride, based on the total dry weight of the compound. By comparison, it is noted that when substantially all of the stoichiometric excess halide (i.e., chloride) has been removed from methylene blue (tetramethylthionine chloride), leaving primarily the chloride anions associated with the cations, the resulting methylene blue derivative contains a one to one molar ratio of cations to anions (in the case of methylene blue this corresponds to approximately 8 wt % chloride), based on its total dry weight. Thus, a "reduced halide-content" compound is intended to mean a compound that has had substantially all of the stoichiometric excess halide anions, as well as at least a portion of the halide anions associated with the cations of the compound, removed. It is noted that the presence of organic halides in the compound are acceptable if the halide atom(s) are not readily hydrolyzed or as long as the compound is not thermally decomposed, either of which would release the halide as an independent entity then capable of producing corrosive effects. Thus, halide which is covalently bonded to the compound is not counted toward the aforesaid ratio of 1 mole of cation to no more than 0.5 moles of halide anion contained in the molecule since covalently bonded halide is not expected to contribute significantly to the corrosion of low nickel content stainless steel alloys.

The term "(meth)acrylic acid," as used herein, is understood to encompass both acrylic acid and methacrylic acid. Similarly, the term "(meth)acrylic acid or its esters" is understood to encompass acrylic acid and methacrylic acid, as well as esters of both.

Although the method of the present invention is described hereinafter in terms of a particular embodiment of inhibiting polymerization of acrylic acid in a distillation process, it is to be understood that the present invention also encompasses methods for inhibiting polymerization of methacrylic acid, as well as esters of acrylic and methacrylic acid, in other contexts, including but not limited to, transport and/or storage of (meth)acrylic acid and its esters.

The method of the present invention will now be described in detail with reference to FIG. 1 which provides a schematic representation of a separation and purification process, such as a distillation process, wherein a crude product stream 10 is fed to distillation apparatus, such as a distillation column 12. In the process depicted in FIG. 1 the purified product is collected at the bottom of the column 12 and lower boiling impurities are removed from the top of the column 12. Persons of ordinary skill in the art will recognize that the present invention is applicable to a further purification process where high boiling impurities are removed from the bottom of a distillation column 12 and purified product is removed from the top of a distillation column 12. As will be recognized by persons of ordinary skill in the art, the distillation apparatus may include more than one distillation unit, or column. For example, some separation and purification processes, employ two or more distillation columns, while others employ an upstream dehydration column followed by a distillation column, and still others use a plurality of columns and other separations units to achieve the desired degree of purification of the crude product streams.

The crude product stream 10 comprises at least one product selected from the group consisting of (meth)acrylic acid and its esters. For example, the crude product stream 10 may include from 20 to 99 wt %, such as 35 to 90 wt %, or even 50 to 80 wt %, of at least one product selected from the group consisting of (meth)acrylic acid and its esters; from 80 to 5 wt %, for example from 65 to 10 wt %, or even from 50 to 20 wt %, of solvent, such as water or a suitable alcohol; and up to 8 wt %, such as up to 6 wt %, or even up to 5 wt %, of co-products, such as, but not limited to, acetic acid.

The distillation column 12 may be any suitable distillation column known in the art. For instance, a packed column, or a sieve tray, valve tray, dual flow tray, or bubble cap tray design, may suitably be used. Within the distillation column 12, the crude product stream 10 is subjected to distillation in the presence of at least one distillation solvent to separate the water from the product, whereby a purified product stream 14 is produced and exits the distillation column 12.

The distillation solvent is introduced to the distillation column 12 via a distillation solvent feed line 16. The distillation solvent or solvents may be any solvent(s) suitable for the distillation of a crude product stream 10 comprising at least one product selected from the group consisting of (meth)acrylic acid and its esters. For example, in one embodiment, the solvent may be substantially water insoluble, generally having a solubility in water at room temperature of 0.5 weight percent or less, preferably 0.2 weight percent or less. Suitable examples of such a water insoluble solvent include, but are not limited to, heptane; heptene; cycloheptane; cycloheptene; cycloheptatriene; methylcyclohexane; ethylcyclopentane; 1,2-dimethylcyclohexane; ethylcyclohexane; toluene; ethylbenzene; ortho-, meta-, or para-xylene; trichloroethylene; trichloropropene; 2,3-dichlorobutane; 1-chloropentane; 1-chlorohexane; and 1-chlorobenzene. In another embodiment, the solvent is selected from ethyl acetate, butyl acetate, dibutyl ether, hexane, heptane, ethyl methacrylate, diethyl ketone, methyl propyl ketone, methyl isobutyl ketone, and methyl tert-butyl ketone. In a further embodiment, the distillation solvent is a mixed solvent which includes at least two solvents. Suitable examples of solvents useful in such mixed solvent include, but are not limited to, diethyl ketone, methyl propyl ketone, methyl isobutyl ketone, methyl tert-butyl ketone isopropyl acetate, n-propyl acetate, toluene, heptane and methylcyclohexane. Toluene is typically used as the distillation solvent.

The crude product stream 10 may be fed to a light ends stripper column (not shown) before being fed to the distillation column 12. The light ends stripper column (not shown) strips light ends, including but not limited to, acrolein, formaldehyde, acetaldehyde, propionaldehyde, methyl ether, and methyl vinyl ketone, from the crude product stream 10. Generally, the stripping gas used is steam. In embodiments where a light ends stripper column (not shown) is employed, the stripped crude product stream 10 exits the bottom of the light ends column (not shown) substantially free of light ends and is then introduced into the distillation column 12.

In accordance with the present invention, a polymerization inhibitor is fed to the distillation column 12 to inhibit polymerization of (meth)acrylic acid and its esters during distillation of the crude product stream 10 and thereafter, during transport and storage.

The polymerization inhibitor comprises at least one reduced halide-content azine dye-based compound. The term "azine dye-based compound," as used herein, refers to a compound having a heterocyclic cation containing six-membered rings having one nitrogen atom (N) and either a sulfur atom (S), an oxygen atom (O), or another nitrogen atom (N), as the only ring heteroatoms; and an anion. More particularly, for example, suitable reduced halide-content azine dye-based compounds have the general formula:

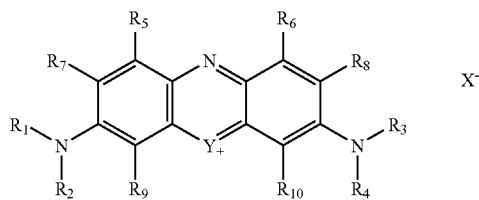

wherein:
Y is selected from the group consisting of S, O, or NR*, where R* is selected from the group consisting of hydrogen, and saturated, unsaturated and other substituted hydrocarbons.
$R_1$-$R_4$ are the same or different from one another; $R_5$-$R_{10}$ are the same or different from one another; and each of $R_1$-$R_{10}$ is selected from the group consisting of hydrogen; saturated, unsaturated and substituted hydrocarbons; and saturated or unsaturated halocarbons.

X comprises at least one mono-, di- or tri-anion in a 1, 1/2, or 1/3 ratio respectively to the cationic component. Where X comprises halide anions, such as one or more of chloride, bromide, iodide or fluoride anions, and the halide anion is present in a ratio of one mole of cation to no more than 0.5 moles of halide anion.

Without limitation, for example, R* may be selected from the group consisting of hydrogen, an aliphatic moiety having from 1 to about 20 carbon atoms, cycloalkyl, aryl, aralkyl, fluoroalkyl, fluoroaryl, fluoroaralkyl, chloroalkyl, or chloroaryl, or chloroaralkyl having from 6 to about 12 carbon atoms.

Similarly, without limitation, $R_1$-$R_4$ may be the same or different and each is selected from the group consisting of hydrogen, an aliphatic moiety having from 1 to about 20 carbon atoms, cycloalkyl, aryl, aralkyl, fluoroalkyl, fluoroaryl, fluoroaralkyl chloroalkyl, chloroaryl, or chloroaralkyl having from 6 to about 12 carbon atoms, heterocyclyl, any alkyl, alkylene, fluoroalkyl, fluoroalkylene chloroalkyl, or chloroalkylene chain being optionally interrupted by one or more hetero atoms. In addition, $R_1$ and $R_2$ together, or $R_3$ and $R_4$ together, may form part of an alicyclic or heterocyclic moiety having from 4 to 10 ring members.

Also without limitation, $R_5$-$R_{10}$ may be the same or different and each is selected from the group consisting of hydrogen, an aliphatic moiety having from 1 to about 20 carbon atoms, cycloalkyl, aryl, aralkyl, fluoroalkyl, fluoroaryl, fluoroaralkyl, chloroalkyl, chloroaryl, or chloroaralkyl having from 6 to about 12 carbon atoms, heterocyclyl, any alkyl or alkylene fluoroalkyl, fluoroalkylene, chloroalkyl, or chloroalkylene chain being optionally interrupted by one or more hetero atoms. In addition, $R_5$ and $R_7$ together, or $R_6$ and $R_8$ together, or $R_1$ and $R_7$ together, or $R_2$ and $R_9$ together, or $R_3$ and $R_8$ together, or $R_{10}$ and $R_4$ together, may form part of an alicyclic or heterocyclic moiety having from 4 to 10 ring members.

With reference to suitable anions, X, the terms "mono-anion", "di-anion", and "tri-anion" refer to the quantitative charge on the anions. More particularly, without limitation, examples of mono-anions would be $HSO_4^-$ and $NO_2^-$; an example of a di-anion would be $SO_4^{2-}$; and an example of a tri-anion would be $PO_4^{3-}$.

Furthermore, anions, X, suitable for use in the present invention may be derived from, nitric acid; sulphuric acid; lower alkanoic, fluoroalconic, or chloroalkanoic (up to C12) acids such as acetic acid and propionic acid; sulfonic acids such as methanesulfonic acid, t-butylsulfonic acid, benzenesulfonic acid, naphthalene sulfonic acid, toluenesulfonic acids, orthophosphoric acid; and phosphonic acids such as benzenephosphonic acid. Other sources which may provide suitable anions, X, include, optionally, tetraphenyl borate derivatives. The anion, X, may be introduced as one or more of a protic acid having a pKa measured in aqueous solution of less than 15. The molar ratio of anion to azine dye-based cation for an anion of given charge z (i.e. $A^{-z}$ would be 1:1/z.

Additionally, for example and without limitation, X may be any anion selected from the group consisting of: $SH^-$; $SO_4^{2-}$; $HSO_4^-$; $RCOO^-$, wherein R is alkyl, cycloalkyl, aryl, aralkyl, heterocyclyl, any alkyl alkyl or alkylene chain being optionally interrupted by one or more hetero atoms, or saturated and unsaturated halocarbons; $RSO_3^-$ (sulfonates), or $ROSO_3^-$ (sulfates), or $RNHSO_3^-$ (sulfamates) wherein R can be an aliphatic moiety having from 1 to about 20 carbon atoms, cycloalkyl, aryl, aralkyl, fluoroalkyl, fluoroaryl, fluoroaralkyl, chloroalkyl, chloroaryl, or chloroaralkyl having from 6 to about 12 carbon atoms, heterocyclyl, any alkyl or alkylene fluoroalkyl, fluoroalkylene chloroalkyl, or chloroalkylene chain being optionally interrupted by one or more hetero atoms; $S^{2-}$; $SO_3^{2-}$; $SCN^-$; $NO_3^-$; $NO_2^-$; $CO_3^{2-}$; $HCO_3^-$; $CN^-$; $HPO_4^{2-}$; $PO_4^{3-}$; $O_2^{2-}$; $HO^-$; and $RO^-$ wherein R is alkyl, cycloalkyl, aryl, aralky, heterocyclyl, any alkyl or alkylene chain being optionally interrupted by one or more hetero atoms, or saturated and unsaturated halocarbons.

The reduced halide-content azine dye-based compound may be used alone, or with other compounds capable of inhibiting polymerization of (meth)acrylic acid and its esters. Such other inhibitor compounds may be water soluble, alcohol soluble, or soluble in organic solvents and include, but are not limited to: hydroquinone (HQ); 4-methoxyphenol (MEHQ); 4-ethoxyphenol; 4-propoxyphenol; 4-butoxyphenol; 4-heptoxyphenol; hydroquinone monobenzylether; 1,2-dihydroxybenzene; 2-methoxyphenol; 2,5-dichlorohydroquinone; 2,5-di-tert-butylhydroquinone; 2-acetylhydroquinone; hydroquinone monobenzoate; 1,4-dimercaptobenzene; 1,2-dimercaptobenzene; 2,3,5-trimethylhydroquinone; 4-aminophenol; 2-aminophenol; 2-N,N-dimethylaminophenol; 2-mercaptophenol; 4-mercaptophenol; catechol monobutylether; 4-ethylaminophenol; 2,3-dihydroxyacetophenone; pyrogallol-1,2-dimethylether; 2-methylthiophenol; t-butyl catechol; di-tert-butylnitroxide; di-tert-amylnitroxide; 2,2,6,6-tetramethyl-piperidinyloxy; 4-hydroxy-2,2,6,6-tetramethyl-piperidinyloxy (4HT); 4-oxo-2,2,6,6-tetramethyl-piperidinyloxy; 4-dimethylamino-2,2,6,6-tetramethyl-piperidinyloxy; 4-amino-2,2,6,6-tetramethyl-piperidinyloxy; 4-ethanoloxy-2,2,6,6-tetramethyl-piperidinyloxy; 2,2,5,5-tetramethyl-pyrrolidinyloxy; 3-amino-2,2,5,5-tetramethyl-pyrrolidinyloxy; 2,2,5,5-tetramethyl-1-oxa-3-azacyclopentyl-3-oxy; 2,2,5,5-tetramethyl-3-pyrrolinyl-1-oxy-3-carboxylic acid; 2,2,3,3,5,5,6,6-octamethyl-1,4-diazacyclohexyl-1,4-dioxy; salts of 4-nitrosophenolate; 2-nitrosophenol; 4-nitrosophenol; copper dimethyldithiocarbamate; copper diethyldithiocarbamate; copper dibutyldithiocarbamate; copper salicylate; iron; phenothiazine (PTZ); 3-oxophenothiazine; 5-oxophenothiazine; phenothiazine dimer; 1,4-benzenediamine; N-(1,4-dimethylpentyl)-N'-phenyl-1,4-benzenediamine; N-(1,3-(dimethylbutyl)-N'-phenyl-1,4-benzenediamine; N-nitrosophenyl hydroxylamine and salts thereof; nitric oxide; nitrosobenzene; p-benzoquinone; copper naphthenate; copper acetate; copper acrylate; manganese dimethyldithiocarbamate; manganese diethyldithiocarbamate; manganese dibutyldithiocarbamate; manganese naphthenate; manganese acetate; manganese acetylacetonate; cobalt acetate; cobalt carbonate; cobalt acetate; nitrogen dioxide; nitrobenzene; nitrosobutane; n-nitrosodiphenylamine; diphenylphenylenediamine; nitrosocarbazole; 1-nitroso-2-naphthol; 2,4 dinitrobenzene; triphenyl phosphine; triethyl phosphine; tributyl phosphine; triphenyl phosphite; triethyl phosphite; tri-i-propylphosphite; tributyl phosphite; tricyclohexyl phosphite; soduim bisulfite; butyl mercaptan; dodecyl mercaptan; N,N-diethylhydroxylamine; N-benzoyl-N-phenylhydroxylamine; benzothiazol-2-yl-thiohydroxylamine; -(benzyloxycarbonyl)hydroxylamine monoethanolamine; 4-phenylenediamine; 3-phenylenediamine; 4-aminodiphenylamine; diphenylamine; di-4-tolylamine; 4-nitrophenylamine; tert-butyl amine; dibenzylamine, acetone oxime; phenyl N-t-butylnitrone; -(4-Pyridyl N-oxide)-N-tert-butylnitrone; isomers thereof; mixtures of two or more thereof; and mixtures of one or more of the above with molecular oxygen. The inhibitor(s) may be used alone or combined with a suitable diluent.

Use of oxygen is preferred when phenolic inhibitors, such as HQ are used, because the oxygen enhances the effectiveness of such phenolic inhibitors. Oxygen may be supplied by adding oxygen-containing gas, such as air, pure oxygen, synthetic air, or any gaseous mixture containing from 0.01 vol % to 100 vol % molecular oxygen, based on the total volume of the oxygen-containing gas, at one or more locations throughout the distillation column 12, or even at various other locations of ancillary equipment (not shown), such as, without limitation, the reboiler, reboiler inlet/outlet, the inlets/outlets of associated pumps, one or more distillation column outlets, or any of the distillation inlets used to supply other materials and compounds.

With reference again to FIG. 1 and the method of the present invention, the reduced halide-content azine-based compound and other inhibitor compounds of the polymerization inhibitor may be introduced to the distillation column 12, separately from one another or mixed together, in one or more inhibitor streams. In addition, such inhibitor streams may enter the distillation column 12 above or below the crude product stream 10, or both above and below the crude product stream 10. Furthermore, it is possible for one or more compounds of the polymerization inhibitor to be introduced into the distillation column 12 simultaneously with, or pre-mixed with, the crude product stream 10.

For example, as shown in FIG. 1, in one embodiment of the present invention, at least one reduced halide-content azine dye-based compound may be fed to the distillation column 12 through a first inhibitor stream 18, while one or more of the other inhibitor compounds are introduced to the distillation column 12 through separate second and third inhibitor streams 20, 22. Optionally, molecular oxygen may be supplied to the distillation column 12, for example, at the bottom of the distillation column 12 through an oxygen feed line 24. One or more of the reduced halide-content azine dye-based compounds and other inhibitor compounds of the polymerization inhibitor may be added to the crude product stream 10 before entry to the distillation column 12. Additionally, one or more of the reduced halide-content azine dye-based compounds and other inhibitor compounds of the polymerization inhibitor may optionally be added to the aqueous distillation column 12 through still another fourth inhibitor stream 26. Various arrangements and methods for feeding the reduced halide-content azine dye-based compounds and other inhibitor compounds to the distillation column 12 are possible and readily determinable by persons of ordinary skill in the relevant art without undue experimentation.

The amounts of (i) the at least one reduced halide-content azine dye-based compound and (ii) the at least one other inhibitor compound that are fed to the distillation column 12 are not especially critical to the method of the present invention and will vary according to which inhibitor compounds are selected for use and the operating conditions under which they are used. It is well within the ability of persons of ordinary skill in the art to determine suitable amounts of the at least one reduced halide-content azine dye-based compound and inhibitor compounds such that polymerization of the product (meth)acrylic acid and its esters is inhibited. For example, without limitation, where the at least one reduced halide-content azine dye-based compound should be added to a product comprising at least one compound selected from the group consisting of (meth) acrylic acid and its esters in an amount such that the resulting product mixture comprises from about 1 to 1,500 ppm, such as from about 50 to about 500 ppm, or even from about 50 to 200 ppm, of the at least one reduced halide-content azine dye-based compound. Similarly, without limitation, at least one other inhibitor compound should be added to a product comprising at least one compound selected from the group consisting of (meth)acrylic acid and its esters in an amount such that the resulting product mixture comprises from about 5 to 10,000 ppm, for example, from about 100 to 8,000 ppm, or even from about 500 to 6,000 ppm, of the at least one other inhibitor compound.

In the context of a purification process such as that shown schematically in FIG. 1, at least one reduced halide-content azine dye-based compound may be introduced to the distillation column 12 such that there is present in the distillation column 12 an amount of from about 1 to 1,500 ppm, such as from about 50 to about 500 ppm, or even from about 50 to 200 ppm, of the at least one reduced halide-content azine dye-based compound, based on the total mass flow of liquid in the purified product stream 14 exiting the distillation column 12. Similarly, without limitation, at least one other inhibitor compound may be provided to the distillation column 12 such that there is present therein an amount of from about 5 to 10,000 ppm, for example, from about 100 to 8,000 ppm, or even from about 500 to 6,000 ppm, of the at least one other inhibitor compound, based on the total mass flow of liquid in the purified product stream 14 exiting the column 12. Where the at least one reduced halide-content azine dye-based compound is added to a product comprising at least one compound selected from the group consisting of Where it is desired to provide molecular oxygen to the distillation column 12, it may be added such that, for example, without limitation, about 0.01 to 5 vol % molecular oxygen is present in the distillation column 12, based on the total volume of the vapor in the distillation column 12. This is also readily determinable by persons of ordinary skill in the art without undue experimentation.

Operating temperatures and pressures impact the flammability limits and oxygen solubility within the purification system, and these properties must be taken into account when determining the appropriate oxygen concentration to be used for the oxygen-containing gas. Considerations of such factors are within the ability of one of ordinary skill in the art, and either pure oxygen or atmospheric air may be commonly employed as the oxygen-containing gas. High oxygen concentrations within the monomer-containing solution itself should be avoided. When oxygen concentrations are large relative to inhibitor concentrations, oxygen can actually increase the rate of polymerization by promoting the formation of peroxides and, ultimately, monomer radicals. For this reason, it is not recommended that oxygen be added when no inhibitor is present. The optimal oxygen to inhibitor ratio will vary with respect to the inhibitor used and is well within the ability of persons having ordinary skill in the art to determine without undue experimentation.

Polymerization inhibitor compounds are generally available as bulk powders and typically, therefore, must be mixed with at least one delivery solvent before introduction into the distillation column 12. As is determinable by persons having ordinary skill in the art, suitable delivery solvents may be aqueous (such as water or a mixture comprising water), or organic (such as an alcohol, acrylic acid, acetic acid, or toluene), and will depend upon the nature of the inhibitor compounds selected.

Thus, in a particular embodiment of the present invention, crude product stream 10 is fed to distillation column 12, along with at least one distillation solvent introduced to the distillation column 12 via distillation solvent feed line 16. Optionally, one or more other inhibitor compounds, along with a suitable delivery solvent, may be introduced to the column through the second and third inhibitor feed lines 20, 22. A purified product stream 14 exits the bottom of the distillation column 12 and is substantially water-free. The purified product stream 14 may be used as is, or it may be further processed, including but not limited, additional distillation to remove specific impurities and further processing to form various grades of purified product.

For example, where the crude product stream 10 comprised acrylic acid, for example, the resulting purified product stream 14 generally has less than 1000, for example less than 800, or even less than 500 ppm of water. Such a purified product stream 14 may also contain nominal amounts of at least one of the following: acetic acid, propionic acid, β-acryloxypropionic acid (AOPA), acrolein, furfural, benzaldehyde, maleic acid, maleic anhydride, protoanemonin, and acetaldehyde.

It is noted that certain distillation column designs, such as a sieve tray column, require use of a vapor phase polymerization inhibitor. Examples of suitable vapor phase inhibitors useful in the present invention include, but are not limited to, n-phenyl hydroxylamine, or derivatives thereof, N-nitrosophenylhydroxylamine and salts thereof, nitric oxide, nitrosobenzene, diethylhydroxylamine and p-benzoquinone. For example, a vapor phase inhibitor may be added to the reboiler and the bottom trays of the column (not shown), while the liquid phase inhibitor is added to the top of the column. The amount of liquid phase inhibitor may range from 1 ppm to 1000 ppm, depending on the feed rate to the column. Such designs are suitable for use in accordance with the process of the present invention.

An overhead distillate stream 28 exits from the top of the distillation column 12 and generally includes, but is not limited to, solutions of water, acetic acid, and/or (meth) acrylic acid and its esters, with the distillation solvent. For instance, where toluene has been utilized as a distillation solvent, solutions of toluene/water, toluene/acetic acid, and toluene/(meth)acrylic acid or its esters, would be produced overhead in a two liquid phase system.

The overhead distillate stream 28 may be phase separated into organic and aqueous phases, and such phase separation may be done by any means known in the art. For example, in one embodiment, the overhead distillate stream 28 is introduced into a tank 30 and allowed to phase separate into an organic phase 32 and an aqueous phase 34. The organic phase 32 predominantly includes the distillation solvent. The aqueous phase 34 includes, but is not limited to, (meth)acrylic acid or its esters, acetic acid, the distillation solvent, and water. In one embodiment, the organic phase 32 is recycled back to the distillation column by way of the solvent feed line 36 so that the distillation solvent may be reused. Also, as indicated in FIG. 1, the aqueous phase 34 exits the tank 30 and at least a portion of it may be recycled (not shown) as wastewater and mixed with upstream process streams (not shown). Although not depicted in FIG. 1, it is to be understood that the aqueous phase 34 may be recycled, in part or completely, and used as feed to another manufacturing process. Alternatively, part or all of the organic and aqueous phases 32, 34, respectively, may be diverted, or treated and released to the environment.

The process of the present invention for preparing reduced halide-content azine dye-based compounds will now be described in detail. As will be readily understood and practicable by persons of ordinary skill in the art, the processes of the present invention for preparing reduced halide-content azine dye-based compounds may be suitably operated as batch processes or continuous processes. The continuous mode of operation is, however, preferred in connection with the processes of the present invention.

A first embodiment of the process of the present invention generally involves converting at least one halide-containing azine dye-based compound to its hydroxide form using a suitable strongly basic ion exchange resin. In this embodiment, the azine dye-based hydroxide compound merely serves as a synthetic intermediate and is subsequently further converted to the reduced halide-content azine dye-based compound by contacting it with a suitable acid compound capable of donating other, desired anions. In a variation of this first embodiment, a strong base ion exchange resin which is in its hydroxide form may be used if it is first converted in a step known as preconditioning, to a corresponding anionic form (using for example a carboxylic acid), before contacting with the at least one halide-containing azine dye-based compound. In another variation of this second embodiment a weak base ion exchange resin in the neutral form may be used if it is first converted, in a step known as preconditioning, to its corresponding anionic form (using for example a carboxylic acid), before contacting with the at least one halide-containing azine dye-based compound More particularly, the first embodiment of the process of the present invention comprises contacting at least one halide-containing azine dye-based compound with a strongly basic anion ion exchange resin capable of absorbing halide anions. This contacting step produces a halide-enriched ion exchange resin and a quantity of azine dye-based compound in the hydroxide form (i.e., an azine dye-based hydroxide compound). Halide-containing azine dye-based compounds suitable for use in the present invention are any azine dye-based compounds as that term is defined hereinabove, and wherein X comprises halide anions in an amount where the ratio of moles of cations to moles of anions is 1 to no more than 0.5. Examples of suitable halide-containing azine dye-based compounds include, but are not limited to, methylene blue (tetramethylthionine chloride), new methylene blue N (basic blue 24), or toluidine blue O (tolonium chloride).

Within no more than about 12 hours, for example, without limitation, within no more than about 60 minutes, of termination of contacting the halide-containing azine dye-based compound with a suitable basic anion ion exchange resin, the quantity of azine dye-based hydroxide compound is then contacted with an acid compound capable of removing the hydroxide anions and donating other, desired anions to form a quantity of reduced halide-content azine dye-based compound having a 1 to no more than 0.5 molar ratio of cations to anions of non-covalently bound halide anions. The other, desired anions may be, for example, without limitation, sulfate anions provided by sulfuric acid, acetate anions provided by acetic acid, maleate anions provided by maleic acid, formate anions provide by formic acid, or phthalate anions provided by phthalic acid.

The time within which the quantity of azine dye-based hydroxide compound is contacted with the acid compound is important because the azine dye-based compound is understood to be susceptible to decomposition while in solution in the hydroxide form under basic (i.e., high pH) conditions, such as a pH greater than about 8. Thus, after contacting with the acid compound, the resulting reduced halide-content azine dye-based compound should have a pH of between about 6 and about 8.

A second embodiment of the process of the present invention generally involves converting at least one halide-containing azine dye-based compound directly to the preferred salt form using a suitable ion exchange resin. In a variation of this second embodiment, where the ion exchange resin is in its hydroxide form, it is first converted in a preconditioning step, to the preferred salt form having the preferred anion species by contacting the resin with an acid capable of providing the preferred anion species. Then, at least one halide-containing azine dye-based compound is contacted with the converted ion exchange resin and is, itself, converted directly to the preferred reduced halide-content azine dye-based compound. In another variation a weakly basic neutral ion exchange resin is first converted in a preconditioning step, to the preferred salt form having the preferred anion species by contacting the resin with an acid capable of providing the preferred anion species. Then, at least one halide-containing azine dye-based compound is contacted with the converted ion exchange resin and is, itself, converted directly to the preferred reduced halide-content azine dye-based compound.

More particularly, the second embodiment of the process of the present invention comprises contacting at least one halide-containing azine dye-based compound with a basic anion ion exchange resin capable of absorbing halide anions and donating other, desired anions to the azine dye-based compound. This contacting step produces a halide-enriched ion exchange resin and a quantity of reduced halide-content azine dye-based compound having a ratio of 1 mole of cations to no more than 0.5 moles of anions of non-covalently bound halide. Halide-containing azine dye-based compounds suitable for use in the present invention are any azine dye-based compounds as that term is defined hereinabove, and wherein X comprises halide anions in a ratio of 1 mole of cations to no more than 0.5 moles of anions. Examples of suitable halide containing azine dye-based compounds include, but are not limited to, methylene blue (tetramethylthionine chloride), new methylene blue N (basic blue 24), or toluidine blue O (tolonium chloride).

Performing the process of the present invention in accordance with the aforesaid second embodiment eliminates the need to titrate with a suitable acid, since the other, desired anions have already been donated directly to the reduced halide-content azine dye-based compound. However, where the basic ion exchange resin does not include the other, desired anion species, a preconditioning step must be employed to first convert the resin, to the desired form, as discussed in further detail hereinafter.

Any strongly or weakly basic anion exchange resin is believed to be suitable for use in the process of the present invention. For example, ion exchange resins based on at least partially cross-linked polymers bearing basic or cationic groups, particularly ammonium groups including quaternary ammonium groups may be successfully used in the process of the present invention.

It is also possible to utilize weak base resins with pendant secondary or tertiary amine groups to convert the halide-containing azine dye-based compounds to another salt intermediate such as acetate or formate.

A particularly preferred group of such basic ion exchange resins are based upon the polymerization product of styrene and divinyl benzene and subsequent functionalization with quaternary ammonium or amine groups. The capacity of the ion exchange resin is not critical although resins with capacities between about 0.8 and 2.2 milliequivalents per milliliter are convenient because they are readily available. The ion exchange resin may be either a gelular (i.e., no permanent porosity) or macroporous type, and, for the strong base anion exchange resin types, may be of either Type 1 or Type 2 functionality. Particularly suitable macroporous, anionic exchange resins are taught in U.S. Pat. No. 4,025,467. These resins are obtained by polymerizing styrene and divinyl benzene in an appropriate ratio in the presence of an appropriate organic solvent, typically followed by halomethylation with agents such as chloro methyl methyl ether, and subsequent amination by halogen displacement with primary, secondary or tertiary amines.

Another class of strong or weak base resins suitable for use in connection with the process of the present invention include polyacrylic resins such as are taught in U.S. Pat. Nos. 2,675,359 and 4,129,534. These resins are obtained by polymerizing an acrylate ester copolymerized with divinyl benzene and a free-radical catalyst in an appropriate ratio in the presence of the appropriate organic solvent. The polyacrylate is then given active groups by reaction with a polyfunctional amine with at least one primary amine group and one secondary or more frequently, a tertiary amine group to form a weak base functionalized resin. The resin can be further derivativized typically via haloalkylation with agents such as chloromethane to generate strongly basic resins.

It may also be possible to generate the desired reduced halide content azine dye-based compounds using a strong acid cation exchange resin wherein the azine cation is associated with a resin-bound sulfate or other appropriate anion. The chloride ion would remain in solution and be washed from the column. The cationic azine-based dye-fragment could then be released from the resin and the resin regenerated to its protonated form upon treatment using a strong acid, such as sulfuric or some other suitable acid.

Other ion exchange resins useful in the process of this invention include ion exchange resins based on a polyvinylpyridine backbone as discussed in U.S. Pat. Nos. 4,221,871 and 5,693,680. These ion exchange resins comprise copolymers of divinylbenzene and vinylpyridine, and which have had a substantial amount of their pyridyl groups converted to 1-(C4 to C8 alkyl)-pyridinium. These ion exchange resins can be prepared by a process which involves post-functionalizing a bead-form copolymer of divinylbenzene and vinylpyridine with an alkylating agent (R-L), wherein R is a branched or unbranched alkyl group and L, is a leaving group of sufficient strength to lead to the quaternization of pyridine.

Commercially available examples of strong base resins that are possible to use are Amberlyst A26 OH, Amberjet 4400, Amberjet 4600, Amberlite IRA400, Amberlite IRA900, Amberlite IRA910, Amberlite IRA958 and Duolite AP143, each of which is available from Rohm and Haas Company of Philadelphia, Pa. In addition, Dow Chemical, located in Midland, Mich., offers suitable strong base ion exchange resins, including, but not limited to, Dowex Monosphere AI-400, Dowex Monosphere 550A (OH), Dowex RPU, Dowex 21K XLT, Dowex 21K 16/30, Dowex 21K 16/20, Dowex Marathon A2 and Dowex Marathon MSA. Bayer of Leverkusen, Germany also sells suitable strong base ion exchange resins under the trade names Lewatit M510 and Lewatit Monoplus MP500. Purolite A600, commercially available from Purolite of Pontyclum, Wales Great Britain, and Reillex HPQ, available from Reilly Industries of Indianapolis, Ind., are also suitable strong base ion exchange resins.

Commercially available examples of weak base resins suitable for use in the process of the present invention are: Amberlyst A21, Amberlyst A23, Amberlyst A24, Duolite A561, and Duolite A7, each available from Rohm and Haas Company; Dowex Monosphere 77 and Dowex Monosphere 66, available from Dow Chemical; Lewatit MP 62, available from Bayer; Purolite A100 available from Purolite; and Reillex 402, Reillex 425, and Reillex HP, each available from Reilly industries.

Strong base ion exchange resins containing quaternary ammonium groups, including both type 1 and type 2 resins, are particularly suitable for use in the process of the present invention, for example, without limitation, the Amberlyst A26 OH (type 1) and Amberjet 4600 (type 2) resins mentioned hereinabove.

Contacting the halide-containing azine dye-based compound with the basic anionic ion exchange resin may be accomplished in any manner known to persons of ordinary skill in the art. For example, without limitation, the ion exchange resin may be placed within a vessel, such is a column constructed of material capable of resisting corrosion or deterioration by halide anions, the azine dye-based compound, caustic rinses, and the basic ion exchange resin. A solution containing the halide-containing azine dye-based compound may then be feed into the vessel at a temperature between 15° C. and 50° C. (preferably at room temperature) such that it passes through and contacts the ion exchange resin. After the halide-containing azine dye-based compound contacts the ion exchange resin, an effluent stream comprising a reduced halide-content product exits the vessel. The effluent stream may then be collected and titrated with acid as described hereinabove to produce the desired derivative having the preferred anion species.

Preconditioning (sometimes also referred to, simply, as conditioning) is used herein to mean the process of converting an ion exchange resin from one form to another (i.e., from a cationic resin having one species of anions to a converted resin having another, or from a neutral amine resin to a cationic ammonium resin with the appropriate anionic group) generating a different species with appropriate associated anions, prior to using it to convert the compound of interest.

For example, where a basic ion exchange resin, which is otherwise suitable for use in the process of the present invention, is not in its hydroxide form (i.e. a resin in the halide form), the resin may be converted to the hydroxide form, prior to contacting halide-containing azine dye-based compounds with it. Preconditioning the ion exchange resin in this manner typically involves contacting the resin with caustic, i.e., a sodium hydroxide solution. The ion exchange resin, now in its hydroxide form, may be rinsed with water to remove any residual caustic, and then contacted with halide-containing azine dye-based compounds, thereby converting the azine dye-based compounds to their hydroxide form.

Similarly, as discussed hereinabove, it is possible to use a basic ion exchange resin which has the capacity to absorb the halide anions of a halide-containing azine dye-based compound and already contains the other, desired anions. Where a basic ion exchange resin is in the hydroxide form, but it is desired to use it in another salt form having the other, desired anion species, it may be converted prior to contacting halide-containing azine dye-based compounds with it, by preconditioning. Preconditioning the ion exchange resin in this manner typically involves contacting the resin with a suitable acid that will provide the desired anion species. For example, as is understood by persons of ordinary skill in the art, acetic acid will provide acetate anions to the resin, and maleic acid will provide maleate anions to the resin. The ion exchange resin, now in its preferred salt form, may be rinsed with water to remove any residual acid, and then contacted with halide-containing azine dye-based compounds, thereby converting the azine dye-based compounds directly to the desired derivative salt form. Use of this preconditioning step in the process of the present invention is useful to avoid handling the relatively unstable-hydroxide form of the azine dye-based compound.

Of course, as an ion exchange resin continues to be contacted with successive amounts of halide-containing azine dye-based compounds, its ability to absorb halide anions and donate hydroxide anions is diminished to the point where it is impractical to continue using it—a point known as exhaustion. Many exhausted basic ion exchange resins suitable for use in the process of the present invention can be regenerated by contacting the exhausted resin with caustic. For example, without limitation, regeneration of exhausted ion exchange resin may typically involve a preliminary step of rinsing the ion exchange resin with water to remove any residual product, and then passing caustic, such as sodium hydroxide solution, through the ion exchange resin, and then rinsing again with water to remove residual caustic from the resin.

It is noted that exhausted ion exchange resins of type 1 are sometimes difficult to regenerate back to the desired hydroxide form by contacting with a caustic solution alone. In such cases, it is sometimes beneficial to perform a preliminary rinse step using bicarbonate, as outlined in U.S. Pat. No. 4,025,467, followed by a caustic rinse step as described hereinabove. Alternatively, a preliminary rinse step using sodium sulfate, as outlined in U.S. Pat. No. 2,723,245, followed by a caustic rinse step as described hereinabove may be used.

It may be observed during the ion exchange resin synthesis of carboxylate anion modified azine dye-based compounds (namely tetramethylthionine derivatives) that these derivatives may have more limited solubility in aqueous solution relative to the corresponding sulfate derivatives. Without intending to be limited by theory, it is suspected that the resulting tetramethylthionine carboxylate salts may have a tendency to precipitate out of aqueous solution and clog the column in procedures where the carboxylate salts were generated, procedures using from 1.5 to about 1.8 wt % aqueous solutions of methylene blue have been observed to he more successful than procedures using 2 to 2.4 wt % solutions. Thus, it is suggested that the aforesaid solubility and precipitation problems may be mitigated by using different solvent mixtures in the ion exchange process, such that the solubility of the product will not hamper the flow of material through the column.

It is noted that, as will be readily understood by persons of ordinary skill in the art, the determination and calculation of the amounts of the resin, caustic and acids required to perform the above-described steps will depend upon the ionization state of the anions involved and the concentrations of various caustic and acid solutions, as well as the amount of halide-containing azine dye-based compounds to be converted.

EXAMPLES

The following Examples 1-9 are provided as illustrations of inhibiting polymerization of (meth)acrylic acid or its esters during separation and purification using a multi-component inhibitor in accordance with the method of the present invention. Extended runs of an azeotropic toluene distillation column were conducted at operating conditions using a 1 inch diameter, 30-tray Oldershaw column mounted on a bottoms reboiler pot sparged with air at a rate of 67 cubic centimeters per minute. The feed tray for the crude product stream, which contained, among other things, acrylic acid, was at tray 20. The control tray was at tray 13. The trays were numbered by counting beginning from the bottom of the column.

Example 1 (Comparative)

(Multi-component Inhibitor System Comprised Hydroquinone and Phenothiazine, without a Reduced Halide-content Azine Dye-based Compound)

An aqueous acrylic acid product stream was purified (i.e., dehydrated) by azeotropic distillation in the aforesaid distillation column tinder the following conditions:
215 mm Hg top pressure
294 g/hr aqueous AA feed rate
490 g/hr toluene reflux rate
92° C. control tray temperature Aqueous acrylic acid was fed to the distillation column at tray 20 and toluene reflux was fed to the top tray at the rate indicated. The aqueous acrylic acid feed stream composition contained 73.6 wt % acrylic acid, 0.8 wt % beta-acryloxypropionic acid (AOPA), 21.9 wt % water, 3.1 wt % acetic acid, and 0.6 wt % other minor components such as formaldehyde, formic acid, maleic acid, and hydroquinone polymerization inhibitor. An inhibitor solution of 1.0 wt % phenothiazine and 1.31 wt % hydroquinone in glacial acrylic acid was fed into the distillation column at trays 15 and 24, each at a rate of 9.9 g/hr. An additional stream of 1.0 wt % phenothiazine and 2.0 wt % hydroquinone in glacial acrylic acid was fed to the top tray at a rate of 0.7 g/hr. The inhibitor feeds resulted in inhibitor levels in the bottoms of approximately 900 ppm phenothiazine and 1500 ppm hydroquinone. Bottoms product was collected at a rate of 240 g/hr and contained 94.8 wt % acrylic acid, 3.7 wt % beta-acryloxypropionic acid, 5760 ppm acetic acid, and <10 ppm toluene. Aqueous distillate was collected at a rate of 74 g/hr and contained 83.0% water, 2.6 wt % acrylic acid, and 14.4 wt % acetic acid.

The column was operated for two eight-hour runs. The amount of polymer deposited in the column at the end of each eight hour run was estimated by visual inspection. Each tray section was examined for size and distribution of polymer. The polymer was rated on a scale from 1 to 5 for size, ranging from 0.7 mm diameter (a rating of 1.0) to 2.8 mm diameter (a rating of 5). The polymer was also rated on a scale of 1 to 5 for distribution, where the numbers indicate the number of particles of the same size. The product of these ratings in each tray section were summed over the entire column to give a total column polymer count. After eight hours on stream the total column polymer count was about 30, and after sixteen hours it was about 31.

Example 2 (Comparative)

(Multi-component Inhibitor System Comprised Methylene Blue, Hydroquinone, and Phenothiazine)

Methylene blue is a thiazine dye-based compound, but is not of reduced halide-content.

An aqueous acrylic acid product stream was purified (i.e., dehydrated) by azeotropic distillation in the aforesaid distillation column under the following conditions:
215 mm Hg top pressure
287 g/hr aqueous AA feed rate
553 g/hr toluene reflux rate
92° C. control tray temperature Aqueous acrylic acid was fed to the distillation column at tray 20 and toluene reflux was fed to the top tray at the rate indicated. The aqueous acrylic acid feed stream composition contained 64.0 wt % acrylic acid, 0.5 wt % beta-acryloxypropionic acid (AOPA), 32.3 wt % water, 2.5 wt % acetic acid, and 0.7 wt % other minor components such as formaldehyde, formic acid, maleic acid, and hydroquinone polymerization inhibitor, based on the total weight of the feed stream. An inhibitor solution of 1.0 wt % phenothiazine and 1.17 wt % hydroquinone in glacial acrylic acid was fed into the distillation column at trays 15 and 24, each at a rate of 9.9 g/hr. An additional stream of 1.0 wt % phenothiazine and 2.0 wt % hydroquinone in glacial acrylic acid was fed to the top tray at a rate of 0.7 g/hr. A solution of 0.44 wt % tetramethylthionine chloride in water was fed to tray 18. The inhibitor feeds resulted in inhibitor levels in the bottoms of approximately 900 ppm phenothiazine, 1500 ppm hydroquinone and 100 ppm tetramethylthionine chloride. Bottoms product was collected at a rate of 213 g/hr and contained 95.3 wt % acrylic acid, 3.0 wt % beta-acryloxypropionic acid, 3400 ppm acetic acid, and <10 ppm toluene. Aqueous distillate was collected at a rate of 99 g/hr and contained 85.8% water, 2.3 wt % acrylic acid, and 11.9 wt % acetic acid. The column was operated for two eight-hour runs. After eight hours on stream the total column polymer count resulting from this Example 2 was about 18, and after 16 hours it was about 12.

Example 3

(Multi-component Inhibitor System Comprised Tetramethylthionine Sulfate, Hydroquinone, and Phenothiazine)

The azeotropic distillation of comparative Example 2 was repeated with the substitution of tetramethylthionine sulfate for tetramethylthionine chloride. Tetramethylthionine sulfate is a reduced halide-content azine dye-based compound of the thiazine dye family of compounds. The aqueous acrylic acid product stream was fed at 293 g/hr and its composition contained 69.1 wt % acrylic acid, 0.9 wt % beta-acryloxypropionic acid (AOPA), 25.2 wt % water, 3.1 wt % acetic acid, and 1.7 wt % other minor components such as formaldehyde, formic acid, maleic acid, and hydroquinone polymerization inhibitor. The toluene reflux was fed to the top tray at a rate of 595 g/hr. An inhibitor solution of 1.0 wt % phenothiazine and 1.30 wt % hydroquinone in glacial acrylic acid was fed into the distillation column at trays 15 and 24, each at a rate of 9.9 g/hr. An additional stream of 1.0 wt % phenothiazine and 2.0 wt % hydroquinone in glacial acrylic acid was fed to the top tray at a rate of 0.7 g/hr. A solution of 0.55 wt % tetramethylthionine sulfate in water was fed to tray 18. The inhibitor feeds resulted in inhibitor levels in the bottoms of approximately 900 ppm phenothiazine, 1500 ppm hydroquinone and 135 ppm tetramethylthionine sulfate. Bottoms product was collected at a rate of 220 g/hr and contained 94.7 wt % acrylic acid, 3.02 wt % beta-acryloxypropionic acid, 4600 ppm acetic acid, and <10 ppm toluene. Aqueous distillate was collected at a rate of 99 g/hr and contained 78.8% water, 2.0 wt % acrylic acid, and 19.2 wt % acetic acid. The column was operated for two eight-hour runs. After eight hours on stream the total column polymer count was about 4, and after sixteen hours it was about 3, which is only about 23% of the polymer count achieved by the methylene blue-containing inhibitor system used in comparative Example 2. In addition, since the tetramethylthionine sulfate was a reduced halide-content compound, a reduction in equipment corrosion was expected.

Example 4

(Multi-component Inhibitor System Comprised Tetramethylthionine Acetate, Hydroquinone, and Phenothiazine)

The azeotropic distillation of comparative Example 2 was repeated with the substitution of tetramethylthionine acetate for tetramethylthionine chloride. Tetramethylthionine acetate is a reduced halide-content azine dye-based compound of the thiazine dye family of compounds. The aqueous acrylic acid was fed at 293 g/hr and its composition contained 69.8 wt % acrylic acid, 0.8 wt % beta-acryloxypropionic acid (AOPA), 24.8 wt % water, 3.0 wt % acetic acid, and 1.6 wt % other minor components such as formaldehyde, formic acid, maleic acid, and hydroquinone polymerization inhibitor. The toluene reflux was fed to the top tray at a rate of 574 g/hr. An inhibitor solution of 1.0 wt % phenothiazine and 1.31 wt % hydroquinone in glacial acrylic acid was fed into the distillation column at trays 15 and 24, each at a rate of 9.9 g/hr. An additional stream of 1.0 wt % phenothiazine and 2.0 wt % hydroquinone in glacial acrylic acid was fed to the top tray at a rate of 0.7 g/hr. A solution of 0.44 wt % tetramethylthionine acetate in water was fed to tray 18. The inhibitor feeds resulted in inhibitor levels in the bottoms of approximately 900 ppm phenothiazine, 1500 ppm hydroquinone and 100 ppm tetramethylthionine acetate. Bottoms product was collected at a rate of 215 g/hr and contained 94.5 wt % acrylic acid, 3.6 wt % beta-acryloxypropionic acid, 4100 ppm acetic acid, and <10 ppm toluene. Aqueous distillate was collected at a rate of 95 g/hr and contained 83.9% water, 2.7 wt % acrylic acid, and 13.5 wt % acetic acid. The column was operated for two eight-hour runs. After eight hours on stream the total column polymer count was about 8, and after sixteen hours it was about 36. Thus, a polymerization inhibitor which comprised tetramethylthionine acetate inhibited polymerization and, since it was of reduced halide-content, a reduction in equipment corrosion was expected.

Example 5

(Multi-component Inhibitor System Comprised Tetramethylthionine Phthalate, Hydroquinone, and Phenothiazine)

The azeotropic distillation of comparative Example 2 was repeated with the substitution of tetramethylthionine phthalate for tetramethylthionine chloride. Tetramethylthionine phthalate is a reduced halide-content azine dye-based compound of the thiazine dye family of compounds. The aqueous acrylic acid was fed at 292 g/hr and its composition contained 69.1 wt % acrylic acid, 0.9 wt % beta-acryloxypropionic acid (AOPA), 25.2 wt % water, 3.1 wt % acetic acid, and 1.7 wt % other minor components such as formaldehyde, formic acid, maleic acid, and hydroquinone polymerization inhibitor. The toluene reflux was fed to the top tray at a rate of 586 g/hr. An inhibitor solution of 1.0 wt % phenothiazine and 1.31 wt % hydroquinone in glacial acrylic acid was fed into the distillation column at trays 15 and 24, each at a rate of 9.9 g/hr. An additional stream of 1.0 wt % phenothiazine and 2.0 wt % hydroquinone in glacial acrylic acid was fed to the top tray at a rate of 0.7 g/hr. A solution of 0.77 wt % tetramethylthionine phthalate in water was fed to tray 18. The inhibitor feeds resulted in inhibitor levels in the bottoms of approximately 900 ppm phenothiazine, 1500 ppm hydroquinone and 185 ppm tetramethylthionine phthalate. Bottoms product was collected at a rate of 224 g/hr and contained 93.6 wt % acrylic acid, 3.0 wt % beta-acryloxypropionic acid, 3770 ppm acetic acid, and <10 ppm toluene. Aqueous distillate was collected at a rate of 94 g/hr and contained 73.8% water, 2.5 wt % acrylic acid, and 23.7 wt % acetic acid. The column was operated for one eight-hour run before flooding required a shutdown and, therefore, a second 8-hour run was not possible under the foregoing conditions. After eight hours on stream the total column polymer count was about 17. Thus, a polymerization inhibitor which comprised tetramethylthionine acetate inhibited polymerization at a level comparable to comparative Example 2 and, since it was of reduced halide-content, a reduction in equipment corrosion was expected.

Example 6 (Comparative)

(Multi-component Inhibitor System Comprised Methylene Blue, Hydroquinone, and Phenothiazine)

The azeotropic distillation of comparative Example 2 was repeated with a higher concentration of tetramethylthionine chloride. The aqueous acrylic acid was fed at 287 g/hr and its composition contained 65.8 wt % acrylic acid, 0.4 wt % beta-acryloxypropionic acid (AOPA), 29.7 wt % water, 2.6 wt % acetic acid, and 1.5 wt % other minor components such as formaldehyde, formic acid, maleic acid, and hydroquinone polymerization inhibitor. The toluene reflux was fed to the top tray at a rate of 459 g/hr. An inhibitor solution of 1.0 wt % phenothiazine and 1.17 wt % hydroquinone in glacial acrylic acid was fed into the distillation column at trays 15 and 24, each at a rate of 9.9 g/hr. An additional stream of 1.0 wt % phenothiazine and 2.0 wt % hydroquinone in glacial acrylic acid was fed to the top tray at a rate of 0.7 g/hr. A solution of 1.32 wt % tetramethylthionine chloride in water was fed to tray 18. The inhibitor feeds resulted in inhibitor levels in the bottoms of approximately 900 ppm phenothiazine, 1500 ppm hydroquinone and 296 ppm tetramethylthionine chloride. Bottoms product was collected at a rate of 216 g/hr and contained 96.6 wt % acrylic acid, 3.0 wt % beta-acryloxypropionic acid, 3650 ppm acetic acid, and <10 ppm toluene. Aqueous distillate was collected at a rate of 96 g/hr and contained 82.6% water, 2.2 wt % acrylic acid, and 15.2 wt % acetic acid. The column was operated for two eight-hour runs. After eight hours on stream the total column polymer count was about 88, and after sixteen hours it was about 40.

Example 7

(Multi-component Inhibitor System Comprised Tetramethylthionine Sulfate, Hydroquinone, and Phenothiazine)

The azeotropic distillation of comparative Example 2 was repeated with the substitution of tetramethylthionine sulfate for tetramethylthionine chloride, but at a higher concentration. The aqueous acrylic acid was fed at 293 g/hr and its composition contained 69.1 wt % acrylic acid, 0.9 wt % beta-acryloxypropionic acid (AOPA), 25.2 wt % water, 3.1 wt % acetic acid, and 1.7% other minor components such as formaldehyde, formic acid, maleic acid, and hydroquinone polymerization inhibitor. The toluene reflux was fed to the top tray at a rate of 587 g/hr. An inhibitor solution of 1.0 wt % phenothiazine and 1.31 wt % hydroquinone in glacial acrylic acid was fed into the distillation column at trays 15 and 24, each at a rate of 9.9 g/hr. An additional stream of 1.0 wt % phenothiazine and 2.0 wt % hydroquinone in glacial acrylic acid was fed to the top tray at a rate of 0.7 g/hr. A solution of 1.0 wt % tetramethylthionine sulfate in water was fed to tray 18. The inhibitor feeds resulted in inhibitor levels in the bottoms of approximately 900 ppm phenothiazine, 1500 ppm hydroquinone and 230 ppm tetramethylthionine sulfate. Bottoms product was collected at a rate of 217 g/hr and contained 93.7 wt % acrylic acid, 3.4 wt % beta-acryloxypropionic acid, 5100 ppm acetic acid, and <10 ppm toluene. Aqueous distillate was collected at a rate of 93 g/hr and contained 78.1% water, 2.3 wt % acrylic acid, and 19.6 wt % acetic acid. The column was operated for one eight-hour run before flooding required a shutdown and, therefore, a second 8-hour run was not possible under the foregoing conditions. After eight hours on stream the total column polymer count was about 29, which is greater than comparative Example 2 and less than comparative Example 6 (which both included tetramethylthionine chloride), but more than Example 3 (which employed a lesser amount of the tetramethylthionine sulfate). Since the tetramethylthionine sulfate was of reduced halide-content, a reduction in equipment corrosion was expected.

Example 8

(Multi-component Inhibitor System Comprised Tetramethylthionine Acetate, Hydroquinone, and Phenothiazine)

The azeotropic distillation of comparative Example 2 was repeated with the substitution of tetramethylthionine acetate for tetramethylthionine chloride. The aqueous acrylic acid was fed at 293 g/hr and its composition contained 75.5 wt % acrylic acid, 0.7 wt % beta-acryloxypropionic acid (AOPA), 20.3 wt % water, 3.0 wt % acetic acid, and 0.5 wt % other minor components such as formaldehyde, formic acid, maleic acid, and hydroquinone polymerization inhibitor. The toluene reflux was fed to the top tray at a rate of 466 g/hr. An inhibitor solution of 1.0 wt % phenothiazine and 1.31 wt % hydroquinone in glacial acrylic acid was fed into the distillation column at trays 15 and 24, each at a rate of 9.9 g/hr. An additional stream of 1.0 wt % phenothiazine and 2.0 wt % hydroquinone in glacial acrylic acid was fed to the top tray at a rate of 0.7 g/hr. A solution of 0.99 wt % tetramethylthionine acetate in water was fed to tray 18. The inhibitor feeds resulted in inhibitor levels in the bottoms of approximately 900 ppm phenothiazine, 1500 ppm hydroquinone and 317 ppm tetramethylthionine acetate. Bottoms product was collected at a rate of 238 g/hr and contained 91.2 wt % acrylic acid, 3.8 wt % beta-acryloxypropionic acid, 6170 ppm acetic acid, and <10 ppm toluene. Aqueous distillate was collected at a rate of 76 g/hr and contained 79.2% water, 2.2 wt % acrylic acid, and 18.6 wt % acetic acid. The column was operated for two eight-hour runs. After eight hours on stream the total column polymer count was about 18, and after sixteen hours it was about 89. Thus, a polymerization inhibitor which comprised tetramethylthionine acetate inhibited polymerization at a level comparable to comparative Example 6 and, since it was of reduced halide-content, a reduction in equipment corrosion was expected.

Example 9

(Multi-component Inhibitor System Comprised Nile Blue A, Hydroquinone, and Phenothiazine)

The azeotropic distillation of comparative Example 2 was repeated with the substitution of 5-amino-4-(diethylamino) benzo[a]phenoxazinium hydrogen sulfate (Nile Blue A) for tetramethylthionine chloride. Nile Blue A is a reduced halide-content azine dye-based compound of the oxazine dye family of compounds. The aqueous acrylic acid was fed at 293 g/hr and its composition contained 72.6 wt % acrylic acid, 0.9 wt % beta-acryloxypropionic acid (AOPA), 21.5 wt % water, 3.2 wt % acetic acid, and 1.8 wt % other minor components such as formaldehyde, formic acid, maleic acid, and hydroquinone polymerization inhibitor. The toluene reflux was fed to the top tray at a rate of 485 g/hr. An inhibitor solution of 1.0 wt % phenothiazine and 1.31 wt % hydroquinone in glacial acrylic acid was fed into the distillation column at trays 15 and 24, each at a rate of 9.9 g/hr. An additional stream of 1.0 wt % phenothiazine and 2.0 wt % hydroquinone in glacial acrylic acid was fed to the top tray at a rate of 0.7 g/hr. A solution of 0.55 wt % Nile Blue A in water was fed to tray 18. The inhibitor feeds resulted in inhibitor levels in the bottoms of approximately 900 ppm phenothiazine, 1500 ppm hydroquinone and 125 ppm Nile Blue A. Bottoms product was collected at a rate of 238 g/hr and contained 94.0 wt % acrylic acid, 2.8 wt % beta-acryloxypropionic acid, 4800 ppm acetic acid, and <10 ppm toluene. Aqueous distillate was collected at a rate of 81 g/hr and contained 73.3% water, 2.4 wt % acrylic acid, and 24.3 wt % acetic acid. The column was operated for two eight-hour runs. After eight hours on stream the total column polymer count was about 7, and after sixteen hours it was about 14. Thus, a polymerization inhibitor which comprised Nile Blue A inhibited polymerization better than comparative Example 2 and, since it was of reduced halide-content, a reduction in equipment corrosion was expected.

The following Examples 10-16 are provided as illustrations of various embodiments of the process in accordance with the present invention, for preparing reduced halide-content azine dye-based compounds.

In Examples 10-11 below, a 2.5 centimeter diameter column, constructed of glass, was loaded with strongly basic ion exchange resins. Using this column and resins, a halide-containing azine dye-based compound, Methylene Blue (tetramethylene thionine chloride), was converted to various reduced halide-content azine dye-based derivatives at room temperature.

Example 10

(Conversion of Methylene Blue to Tetramethylthionine Sulfate)

Amberlyst A26 OH (58.35 g), a macroporous Type 1 strongly basic ion exchange resin in the hydroxide form, was added to the 2.5 cm column. The ion exchange resin was rinsed with 160 mL of deionized water at a rate of 10.7 mL/min to give a bed volume of 70.78 mL. A 2.2 wt % aqueous solution of methylene blue (with nominally 2438 ppm chloride ion concentration) was passed through the column and contacted with the ion exchange resin, at a feed rate of 10.70 mL/min. Fractions of the resulting effluent containing tetramethylthionine hydroxide were collected and immediately titrated from a pH of 12.2 to between 6 and 8 with concentrated sulfuric acid. The material generated was 2.08 wt % in tetramethylthionine sulfate ("TMTS") and <1 ppm in chloride on a wet basis. The resulting TMTS contained a ratio of 1 mole of tetramethylthionine cation to $4.5 \times 10^{-3}$ moles of chloride anion (i.e., a ratio of 1 mole of cations to no more than 0.5 moles of anions).

After the ion exchange resin bed was exhausted, the 160 mL of water was passed through the column to purge residual TMTS product from the column. About 800 mL of an 8 wt % solution of bicarbonate in deionized water was passed through the column at a rate of 4.2 mL/min. Afterwards the ion exchange resin was rinsed of the excess bicarbonate using about 160 mL of deionized water at a rate of 10.7 mL/min. The column was then regenerated to the hydroxide form by passing 260 mL of 2N caustic at a rate of 2.6 mL/min afterwards the resin was rinsed of the excess caustic using about 160 mL of deionized water at a rate of 10.7 mL/min. The resin was then ready for use in another exhaustion cycle.

Example 11

Amberjet 4600 (54.32 g), a gelular Type 2 strongly basic ion exchange resin in the chloride form, was added to the 2.5 cm glass column. The ion exchange resin was first rinsed with 160 mL of deionized water at a rate of 10.7 mL/min to give a bed volume of 37 mL. Then, about 560 mL of a 2N aqueous sodium hydroxide solution was passed through the column, to convert the ion exchange resin to the hydroxide form, at a rate between 6.7 to 7.3 mL/min. The resin was then rinsed with 160 mL of deionized water, at a rate of 10.7 mL/min, to remove the excess sodium hydroxide solution from the column.

A 2.4 wt % aqueous solution of methylene blue (with nominally 2660 ppm chloride ion concentration) was then passed through the column and contacted with the ion exchange resin, at a feed rate of 7 mL/min. Fractions of the resulting effluent containing tetramethylthionine hydroxide were collected and immediately titrated from a pH of 12.2-12.4 to between 6 and 8 with concentrated sulfuric acid. The material generated was 2.08 wt % TMTS and 6.2 ppm chloride on a wet basis. The TMTS contained a ratio of 1 mole of tetramethylthionine cation to $2.8 \times 10^{-3}$ moles of chloride anion (i.e., a ratio of 1 mole of cations to no more than 0.5 moles of anions).

After the ion exchange resin was exhausted, 160 mL of deionized water was passed through the column to purge residual TMTS product from the column. The exhausted ion exchange resin was then regenerated back to the hydroxide form using the method described above in Example 10 and the resin was suitable for another exhaustion.

In Examples 12-14 below, a 1 centimeter diameter glass burette was loaded with macroporous Type 1 strongly basic ion exchange resin, Amberlyst A26 OH, in the hydroxide form. The resin is then converted from the hydroxide form to a form having selected anion species, and a halide-containing azine dye-based compound, Methylene Blue (tetramethylenethionine chloride), was converted to various reduced halide-content azine dye-based derivatives having the selected anions at room temperature.

Example 12

(Strongly Basic Resin with Preconditioning with Acetic Acid)

Amberlyst A26 OH ion exchange resin (17 g) was loaded to a 1 cm glass burette. The ion exchange resin was conditioned by passing 69.2 g of a 4% aqueous acetic acid solution through the burette, converting the ion exchange resin from the hydroxide form to the acetate form. The converted ion exchange resin was then rinsed with 250 mL of deionized water where the pH of the resulting wash effluent was 7.

Methylene blue (1.5 wt % aqueous solution, with nominally 1662 ppm chloride) was passed through the glass burette, contacting the ion exchange resin, at a flow rate of 3.2 mL/min. The resulting product material was a reduced halide-content azine dye-based compound, tetramethylthionine acetate (1.29 wt % with 1.8 ppm chloride on a wet basis. The tetramethylthionine acetate contained a ratio of 1 mole of tetramethylthionine cation to $1.35 \times 10^{-3}$ moles of chloride anion (i.e., a ratio of 1 mole of cations to no more than 0.5 moles of anions).

Example 13

(Strongly Basic Resin with Preconditioning with Formic Acid)

Amberlyst A26 OH (17 g) ion exchange resin was loaded to a 1 cm glass burette. The ion exchange resin was conditioned by passing 69.2 g of a 4 wt % aqueous formic acid solution through the burette to convert the ion exchange resin from the hydroxide form to the formate form. The ion exchange resin was then rinsed with 250 mL of deionized water where the pH of the resulting wash effluent was 7.

Methylene blue (1.78 wt % aqueous solution, nominally with 1405 ppm chloride) was passed through the burette, contacting the ion exchange resin, at a flow rate of 3.2 mL/min. The resulting product material was a reduced halide-content azine dye-based compound, tetramethylthionine formate (1.78 wt % with 2.2 ppm chloride on a wet basis). The tetramethylthionine formate contained 1 mole of tetramethylthionine cation to $1.12 \times 10^{-3}$ moles of chloride anion (i.e., a ratio of 1 mole of cations to no more than 0.5 moles of anions).

Example 14

(Strongly Basic Resin with Preconditioning with Maleic Acid)

Amberlyst A26 OH ion exchange resin (17 g) was loaded to a 1 cm glass burette. The ion exchange resin was conditioned with 69.2 g of a 4 wt % aqueous maleic acid solution through the burette to convert the resin to the maleate form. The ion exchange resin was then rinsed with 250 mL of deionized water where the pH of the resulting wash effluent was 3-4.

Methylene blue (1.78 wt % aqueous solution, with nominally 1405 ppm chloride) was passed through the burette, contacting the ion exchange resin, at a flow rate of 3.2 mL/min. The resulting product material was a reduced halide-content azine dye-based compound, tetramethylthionine maleate (2.16 wt % with 2.2 ppm chloride on a wet basis). The tetramethylthionine maleate contained 1 mole of tetramethylthionine cations to $1.15 \times 10^{-3}$ moles of chloride anion (i.e., a ratio of 1 mole of cations to no more than 0.5 moles of anions).

In Example 15 below, a 1 centimeter diameter glass burette was loaded with weakly basic ion exchange resin, Amberlyst 21. The resin, which is normally supplied in the free-base form, is then converted to a form having selected anion species, and a halide-containing azine dye-based compound, Methylene Blue (tetramethylene thionine chloride), is converted at room temperature to various reduced halide-content azine dye-based derivatives having the selected anions.

Example 15

(Weakly Basic Resin with Preconditioning with Acetic Acid)

Amberlyst A21 (about 20.5 g or 31 mL) ion exchange resin was loaded into a 1 cm diameter glass burette. A nominally 50 mL of a 7% aqueous acetic acid solution was passed through the ion exchange resin at 2.08 mL/min followed by 125 mL of deionized water.

A 1.5 wt % aqueous methylene blue solution (containing nominally 1662 ppm chloride) was passed through the burette, contacting the ion exchange resin, at 2.08 mL/min. The product material generated was a reduced halide-content azine dye-based compound, a 1.53 wt % tetramethylthionine acetate aqueous solution containing 9.9 ppm chloride on a wet basis. The tetramethylthionine acetate contained 1 mole of tetramethylthionine cation to $6.27 \times 10^{-3}$ moles of chloride anion (i.e., a ratio of 1 mole of cations to no more than 0.5 moles of anions).

Example 16

(Batch Reaction Using a Strong Base Gelatinous Type 1 Resin)

Amberjet 4400 OH (20.21 g) was charged to a 500 mL flask. Then 205.4 g of 1.96 wt % methylene blue solution (containing nominally 2173 ppm chloride) was charged to the flask to initiate the reaction. The reaction mixture was stirred with a mechanical stirrer at 400 rpm at room temperature during the course of the reaction. Samples (~15 mL) were withdrawn every 15 minutes during the first hour and had a nominal pH of ~12. Each fraction (i.e., sample) was back titrated with sulfuric acid to a pH of 4.5. The concentration of the TMTS samples withdrawn were all similar at 1.35 wt % (68.9% yield) and they contained nominally 32 ppm chloride ion. The resulting TMTS product solution contained 1 mole of tetramethylthionine, cation to $2.22 \times 10^{-2}$ moles of chloride anion (i.e., a ratio of 1 mole of cations to no more than 0.5 moles of anions).

What is claimed is:

1. A method for inhibiting polymerization of (meth) acrylic acid and its esters, comprising the steps of:
   (A) providing a product comprising at least one compound selected from the group consisting of (meth) acrylic acid and its esters; and
   (B) adding an amount of a polymerization inhibitor to said product, said amount being sufficient to inhibit polymerization of said product and said polymerization inhibitor comprising at least one reduced halide-content azine dye-based compound having a cationic component and an anionic component wherein said at least one reduced halide-content azine dye-based compound has the general formula:

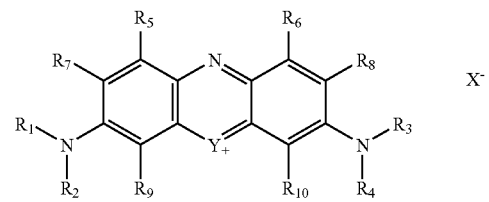

wherein
   Y is selected from the group consisting of S, O, or NR*, where R* is selected from the group consisting of hydrogen, and saturated, unsaturated and substituted hydrocarbons;
   $R_1$-$R_4$ are the same or different from one another; $R_5$-$R_{10}$ are the same or different from one another; and each of $R_1$-$R_{10}$ is selected from the group consisting of hydrogen, and saturated, unsaturated and substituted hydrocarbons; and
   X comprises at least one mono-, di- or tri-anion in a 1, 1/2, or 1/3 ratio respectively to the cationic component.

2. The method according to claim 1, wherein X is selected from the group consisting of: $SH^-$; $SO_4^{2-}$; $HSO_4^-$; $RCOO^-$, wherein R is alkyl, cycloalkyl, aryl, aralkyl, heterocyclyl, any alkyl alkyl or alkylene chain being optionally interrupted by one or more hetero atoms, or saturated and unsaturated halocarbons; $RSO_3^-$ (sulfonates), or $ROSO_3^-$ (sulfates), or $RNHSO_3^-$ (sulfamates) wherein R can be an aliphatic moiety having from 1 to about 20 carbon atoms, cycloalkyl, aryl, aralkyl, fluoroalkyl, fluoroaryl, fluoroaralkyl, chloroalkyl, chloroaryl, or chloroaralkyl having from 6 to about 12 carbon atoms, heterocyclyl, any alkyl or alkylene fluoroalkyl, fluoroalkylene chloroalkyl, or chloroalkylene chain being optionally interrupted by one or more hetero atoms; $S^{2-}$; $SO_3^{2-}$; $SCN^-$; $NO_3^-$; $NO_2^-$; $CO_3^{2-}$; $HCO_3^-$; $CN^{-1}$; $HPO_4^{2-}$; $PO_4^{3-}$; $O_2^{2-}$; $HO^-$; and $RO^-$ wherein R is alkyl, cycloalkyl, aryl, aralky, heterocyclyl, any alkyl or alkylene chain being optionally interrupted by one or more hetero atoms, or saturated and unsaturated halocarbons.

3. The method according to claim 1, wherein said reduced halide-content azine dye-based compound is selected from the group consisting of: tetramethylthionine sulfate, tetramethylthionine acetate, tetramethylthionine maleate, tetramethylthionine formate, and tetramethylthionine phthalate.

4. The method of claim 1, wherein said polymerization inhibitor further comprises at least one additional compound capable of inhibiting polymerization of (meth)acrylic acid and its esters.

5. The method of claim 1, further comprising the steps of wherein said product is purified using distillation apparatus, said method comprising:
  (C) introducing said product to said distillation apparatus;
  (D) introducing said polymerization inhibitor to said distillation apparatus; and
  (E) distilling said product in said distillation apparatus, in the presence of said polymerization inhibitor, to form a purified product.

* * * * *